United States Patent [19]

Shofner et al.

[11] Patent Number: 4,885,473
[45] Date of Patent: Dec. 5, 1989

[54] METHOD AND APPARATUS FOR DETECTING PARTICLES IN A FLUID USING A SCANNING BEAM

[75] Inventors: Frederick M. Shofner; Arthur C. Miller, Jr.; Gerhard Kreikebaum, all of Knoxville, Tenn.

[73] Assignee: Shofner Engineering Associates, Inc., Knoxville, Tenn.

[21] Appl. No.: 188,500

[22] Filed: Apr. 29, 1988

[51] Int. Cl.$^4$ .......................................... G01N 15/06
[52] U.S. Cl. .................................... 250/574; 356/339
[58] Field of Search ............... 356/336, 338, 339, 340, 356/341, 342; 250/574

[56] References Cited

U.S. PATENT DOCUMENTS

| | | | |
|---|---|---|---|
| 3,279,305 | 3/1962 | Akinor et al. | 356/442 |
| 3,603,689 | 10/1969 | Shelnutt | 356/340 |
| 3,797,937 | 3/1974 | Shofner | 356/102 |
| 3,879,615 | 4/1975 | Moser | 250/574 |
| 4,249,244 | 2/1981 | Shofner et al. | 364/525 |
| 4,396,286 | 8/1983 | Shofner et al. | 356/243 |
| 4,473,296 | 9/1984 | Shofner et al. | 356/336 |
| 4,697,925 | 10/1987 | Hyodo et al. | 356/339 |

OTHER PUBLICATIONS

Technical Paper, (6/6/87, San Francisco), entitled "An Inline Optical Particle Counter for High Purity Pressurized Gases", Authors—Gerhard Kreikebaum, Arthur C. Miller, Jr., and Frederick M. Shofner.
Brochure—(5/88)—PPM's Aerosol Scanner.
Brochure—(10/87)—PPM's Handheld Aerosol Monitor.
Brochure—(10/87)—PPM's Multiple Sensor Continuous Aerosol Monitor Cam—TX.

*Primary Examiner*—David C. Nelms
*Attorney, Agent, or Firm*—Luedeka, Hodges & Neely

[57] ABSTRACT

An apparatus and method for detecting particles in a clean environment provides for forming a beam of electromagnetic radiation into an instantaneous scattering volume and scanning the scattering volume in space defined by a flow cell. Particles are transported by fluid means into the space occupied by the scattering volume and individual particles are multiply scanned while passing through the scanning scattering volume. A fluid conduit is provided to transport the fluid and the particles and windows are provided to transmit the radiation beam into the space defined by the flow cell and to transmit scattered radiation from the particles out of the space. The radiation from the particles is collected and detected to provide an output signal. In the preferred embodiment, the output signal is analyzed to determine the concentration of the particles in the fluid and to determine the size and velocity of each individual particle.

19 Claims, 4 Drawing Sheets

METHOD AND APPARATUS FOR DETECTING PARTICLES IN A FLUID USING A SCANNING BEAM

FIELD OF THE INVENTION

This invention is in the field o detecting particles in fluids and more specifically the invention provides a method and apparatus for scanning a sample volume in "clean" gases containing particles to produce light scattering from the particles.

BACKGROUND AND SUMMARY OF INVENTION

In a preferred embodiment of the present invention, a properly-formed, thin beam of electro-magnetic radiation, or light filament, is rapidly scanned through space at velocities generally perpendicular and very high relative to the velocities of particles which are transported by fluid movement. The locus of the light filament movement can be described as a volume in space through which the particles pass, and during such passage, the particles generate light scattering signals which are measured by an electro-optical detector. The detection response to the scattering signals is preferably from a limited region, or scattering volume, or sensitive volume. We prefer the designation scattering volume and use it exclusively hereinafter. Whereas, typically, the thickness of the scattering volume is small compared to its transverse dimension, it is large compared to the dimensions of the particles being measured. Illustrative dimensions are transverse 1cm, thickness 0.01cm, and particle size 0.0001cm.

Present day concerns for microcontamination of process fluids, such as gases in semiconductor manufacturing, require the detection of fine particles having diameters in the range of 0.1 to 10 micrometers (0.00001 & 0.001 cm), in very clean gases having perhaps 10-100 such particles per cubic foot (0.0004 to 0.004/cm$^3$) for illustrative example. To achieve adequate detection sensitivities and counting rates with commonly-available sources of electro-magnetic radiation, such as lasers, it is found that conflicting requirements arise. In very clean environments, the aerosol number density is low. For good statistics one requires large volumetric sampling rates and therefore large scattering volumes. The requirement of large scattering volume leads to larger laser beams and thus to reduced beam intensity and increased minimum particle size detection. It also leads to increased interference from radiation scattered by the far more numerous molecules comprising the fluid by which the aerosols are transported. This also increases minimum particle size detection.

In prior art stationary beam devices, these conflicting requirements of reducing minimum detectable particle size and increasing volumetric sampling rate result in severe problems. As the physical features of semiconductor circuitry necessarily decrease, the particles which will cause a "kill-defect" necessarily decrease both in size and concentration. Hence, prior art instruments do not provide satisfactory information.

The scanning scattering volume of our invention alleviates these problems and, in one preferred embodiment, enables substantially increased volumetric sampling rates while retaining the same minimum detectable size. In another embodiment substantially smaller minimum detectable particle size is achievable while retaining the same sampling rate as prior art stationary beam counters.

In addition, the preferred form of the present invention provides 100% coverage of a conduit or pipe in which the fluid is transported without reducing the diameter of the pipe. Some prior art devices require significant reductions in cross section of the pipe in order to transport the aerosols through a small stationary beam at high speed, leading to size-dependent losses. Other prior art devices do not use flow constrictions but rather electro-optically define a small scattering volume which covers a very small percentage of the cross-sectional area. Accordingly, both such stationary beam device designs necessarily have low true volumetric sampling rate.

Finally, the present invention in its preferred embodiment also provides improvement of the E-0 response function. All electro-optical counters respond imperfectly in the sense that particles of a unique size do not produce precisely unique output responses such as pulses in scattered photon flux, photo current, or voltage. Because the scanning method can produce multiple "hits" upon or "scans" of a particle as it traverses the scattering volume, a better response function can be achieved.

In accordance with a preferred embodiment of the present invention an apparatus is provided for detecting particles in a fluid. The apparatus includes a flow cell and windows are formed in the flow cell for admitting light beam(s) and receiving scattered light signals. A conduit directs a flow of fluid and particles in a path through the flow cell. A source of radiation is provided for producing a radiation beam. A scanning device, preferably a scanning mirror, produces a scanning radiation beam and the scanning beam moves between at least first and second scan positions at a high scan velocity. The scanning beam is directed by an optical system through a window into the chamber and into the path of the fluid and particles. When a particle is scanned over or "hit" by the scanning beam, a scattered light signal is produced. This light is collected by an optical system and is caused to fall on a photosensitive detector which produces a detection signal corresponding to the scattered light. In the preferred embodiment, the detection signal is analyzed by a computer to determine the concentration of particles passing through the scattering volume and to further determine the size and velocity of each particle that is counted.

BRIEF DESCRIPTION OF THE DRAWINGS

Whereas the above describes the field, the problems of prior art stationary beams devices and the general features of the present invention, we now describe a preferred embodiment thereof. This description is for illustration and not limitation of the method or apparatus of the present invention, and it may best be understood by reference to the Drawings in which.

DETAILED DESCRIPTION

Figure 1:
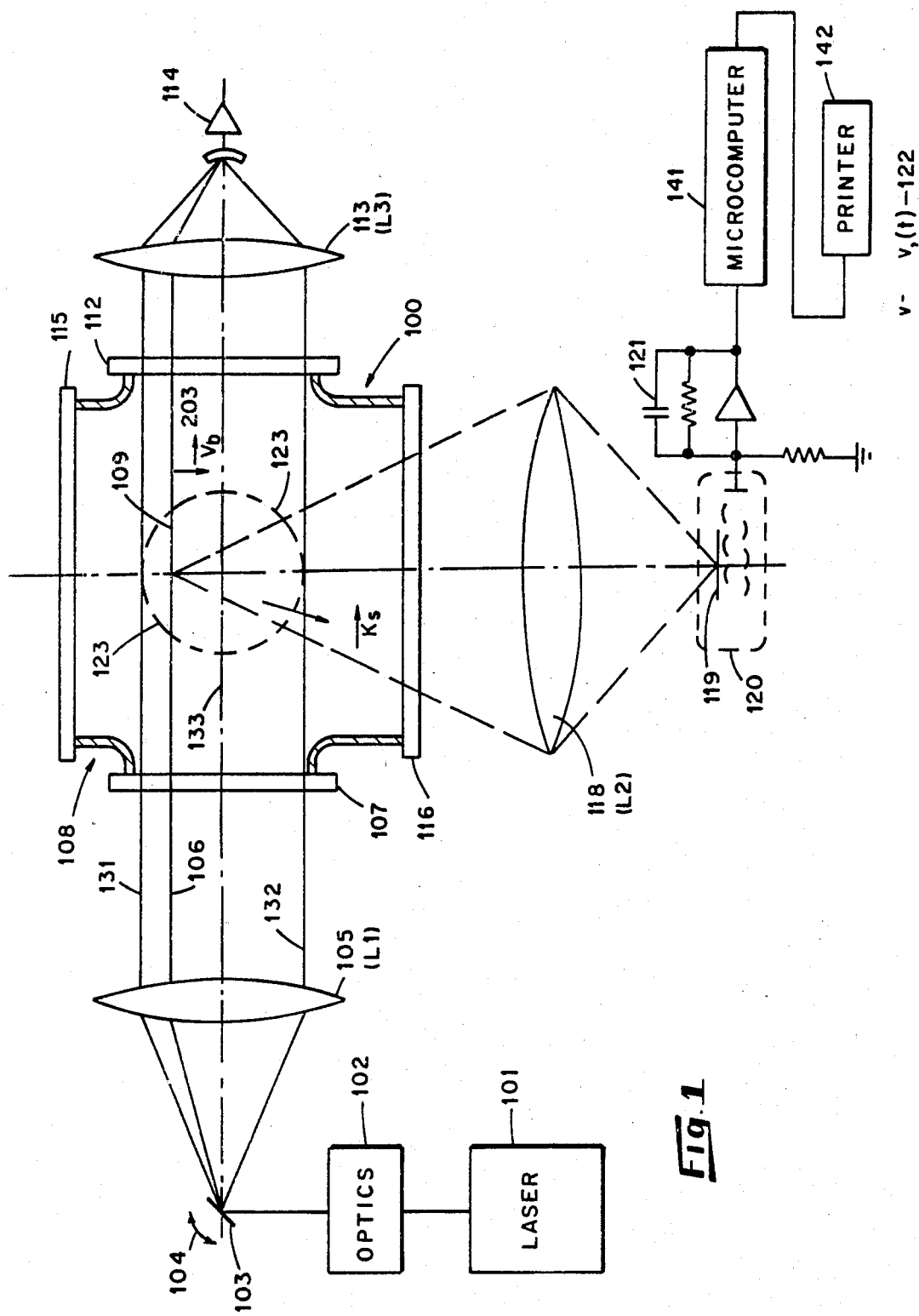
FIG. 1 is a combined physical and schematic drawing illustrating a top, cross-sectional view of an embodiment of the scanning scattering volume method of the present invention.
Figure 2:
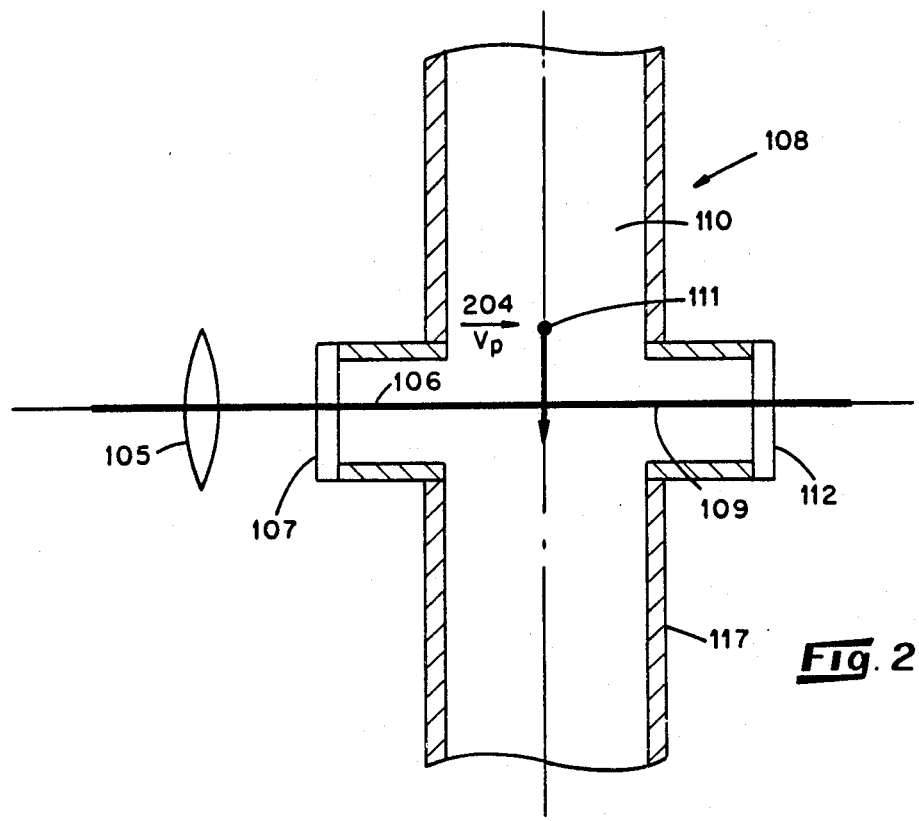
FIG. 2 is an elevation view of the flow cell.

Referring now to FIGS. 1 AND 2, there is shown a top view in FIG. 1 and a side view in FIG. 2 of a scanning beam particle detector 100 embodying a preferred form of the invention. In FIG. 1 electro-magnetic radiation in the visible spectrum from a laser 101 is preformed with conventional first-beam-forming optics 102 into a suitable beam 103. After passage through L1 (105), the filamentary beam is altered in direction and shape 106, as discussed below, and passes through a first isolating window 107, of the flow cell 108.

The instantaneous scattering volume 109 in FIGS. 1 and 2 is defined in the fluid 110 which transports the particles to be measured 111. The fluid may exist in any state of pressure, temperature, composition, etc., that is compatible with the materials of construction and operation of the method. The fluid may move at any velocity but response function results are superior if the velocity is kept below a certain value which depends on the apparatus design parameters. The beam thus defining the instantaneous scattering volume 109 then passes through window 112 to lens L3 113 and Onto a beam power monitor 114.

It is seen from FIGS. 1 and 2 that the flow cell 108 is comprised of windows 107, 112, 115, and 116 and suitable-connected piping 117 which isolate and permit transport of the fluid under test 110. It is further seen that the scanning laser beam 106 covers 100% of the cross-section of flow cell pipe 117 but, of course, less than 100% coverage may be used if desired. Two instantaneous extreme scan positions 131, 132 are shown in FIG. 1 along with typical position 106. It is not essential that the scan lines 106, 131, and 132 be parallel to the centerline 133.

As particles 111 are transported down the flow cell 108 and scanned over or "hit" by the scanning beam 106, light is scattered in all directions. In this embodiment, that light scattered at nominally 90 degrees is caused by collection optics L2 118 to fall on photo detection surface 119. This photodetection surface 119 is preferably the photoemissive cathode of a photomultiplier tube 120 or the photoconductive junction of a silicon photodiode. In any case, photodetection is followed by a first stage of signal processing, shown as a current to voltage preamplifier 121 in FIG. 1. Other first signal processing means, such as charge-sensitive preamplification may obviously be used.

This first stage of signal processing 121 yields a voltage signal v(t) 122 which contains the information of interest in our method. Further processing steps are application- and apparatus-specific.

To better understand the invention it is advantageous to more thoroughly describe and specify the details of the scanning scattering volume 109 in its preferred form and the nature of light-scattering signals v(t) 122 produced thereby. W will initially ignore noise signals and assume $v_1(t)$ faithfully follows the scattered light signals.

First, considering the clean environment in which detector 100 normally operates, it is highly probable that no more than one particle of interest will be in the total scattering volume at any instant. The total scattering volume is the locus of all instantaneous scattering volumes 109 as they are continuously scanned across the flow cell cross section as 123. The diameter of this cross-section 123 represents the transverse dimension described above of order 1cm. A typical beam thickness is of order 0.01cm, giving a total scattering volume of roughly 0.01cm3. Microcontamination particle number densities of interest are typically lower than 100 per standard cubic foot or 0.0035/cm3. Thus the probability of single particle occupancy in the total scattering volume is $$p(1) = 0.01 \times 0.0035 = 3.5 \times 10-5. \quad (1)$$

Obviously, p(1) for the instantaneous volume is much much smaller. Indeed, consideration of Equation 1 and the very low values for p(1) reveals why increased volumetric sampling rate is so urgently needed.

Figure 3:
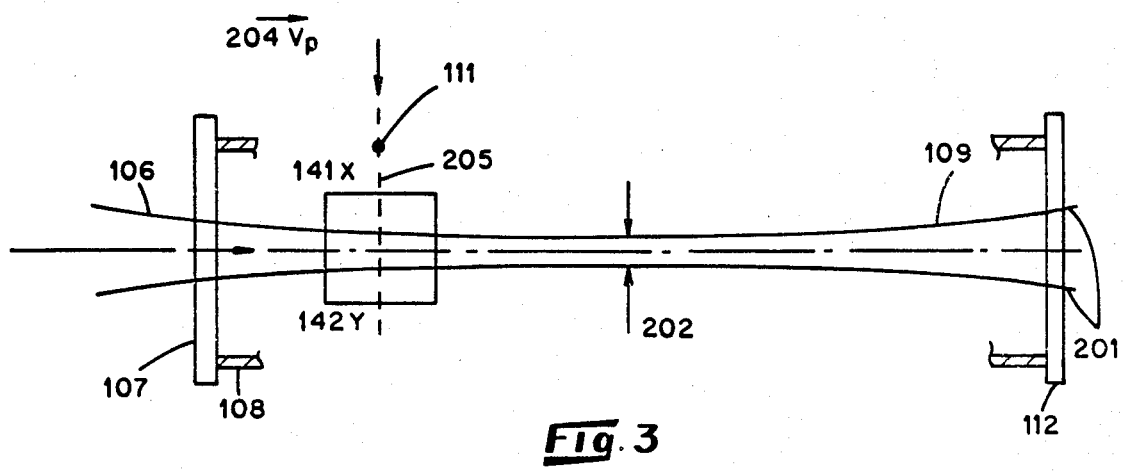
FIG. 3 is an enlarged cross-sectional elevation view of the flow cell which shows the fundamental curved nature of the filamentary or Gaussian beam at an instant in time.
Figure 4:
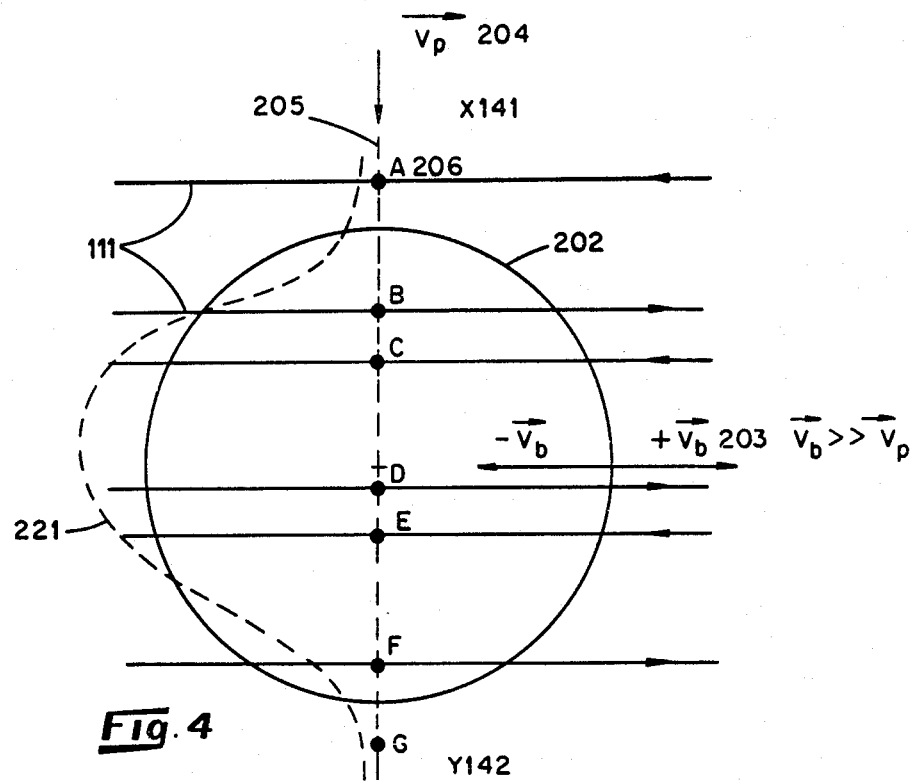
FIG. 4 illustrates the relationship of velocity to the scanning beam at several scan intervals.
Figure 5:
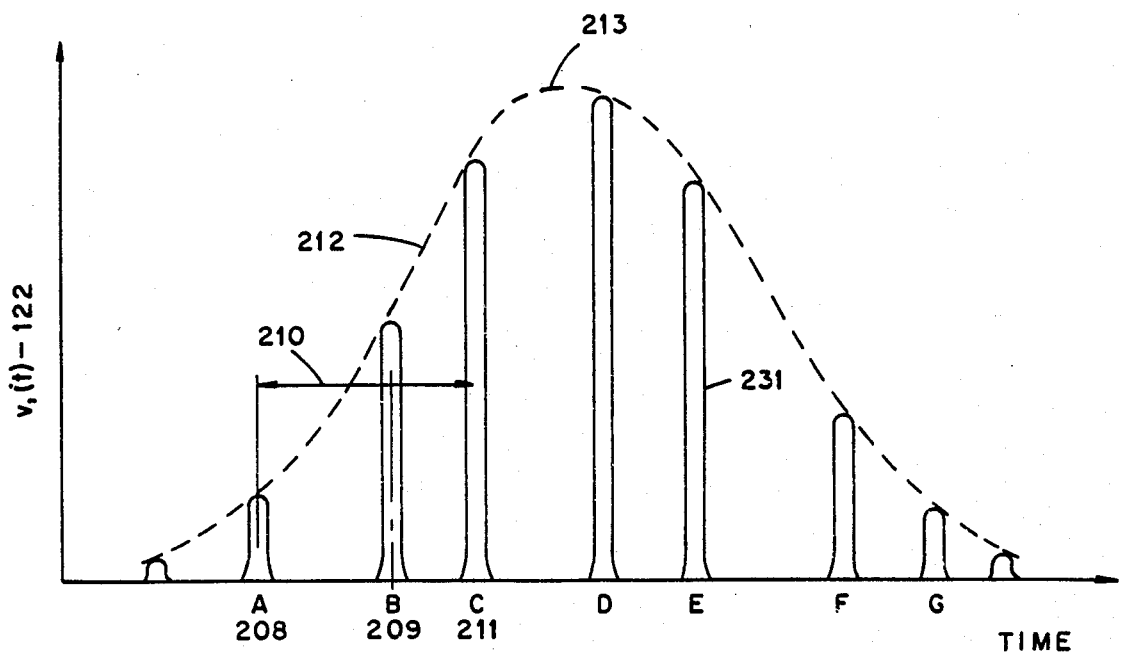
FIG. 5 describes the pulse train produced by multiple scans over a single particle as it passes through the scanning sampling volume.

Referring now to FIGS. 3, 4, and 5 there is shown in FIG. 3 a schematic elevation view of the laser beam 106 and the instantaneous scattering volume 109; in FIG. 4, an enlarged cross-sectional view of the laser beam 106 in scattering volume 109 taken through section lines x-y (141, 142) of FIG. 3; and in FIG. 5, a graph of voltage versus time pulse train, where the voltage $v_1(t)$ 122 represents light scattered by a particle 111 when scanned or "hit" by beam 106 in the scattering volume 109. FIGS. 1, 2 and 3 show the instantaneous scattering volume 109 at a typical transverse scan position represented by the beam 106. In the detailed elevation view of FIG. 3, the laser beam 106 passes through window 107 into the flow cell 108 and has the indicated side view form for the instantaneous scattering volume 109. The exaggerated curves 201 represent so-called "$1/e^2$ waist" profiles as now explained.

It is a result of coherent electromagnetic field theory and measurements that radiation is focused by a lens not to a "point" but a waist 202. This is a parametric description of the beam's "diameter" and constitutes the points at which the intensity is $1/e^2$ times the centerline maximum. For applications of this preferred embodiment this minimum or waist diameter 202 may be of the order of 100 micrometers =0.01cm. The dimension of waist 202 increases prior to and following the minimum at the waist 202 but by proper design may be kept to within prescribed limits, say, +10% over the waist minimums. This waist minimum occurs at the same point as the geometrical optics "focal point". The $1/e^2$ intensity profiles 201 in FIGS. 2a are exaggerated to clearly indicate their fundamental curvature. In the preferred embodiment, the beam is more cylindrical or filamentary in the scattering volume.

In the further-enlarged axial view x-y of FIG. 4, a circle illustrates the parametric laser beam waist 202 (hereafter assumed constant), the beam scan velocity Vb 203, and the particle's velocity Vp 204 and trajectory 205. The beam scan velocity Vb 203 is horizontally both to the left and right in this embodiment and is much larger than the particle velocity Vp 204. Obviously, other beams shapes other than circular may be used.

During scanning of the scattering volume 202 over a particle 111, photons are scattered in all directions. As for stationary beam counters, this radiation may be collected in a forward, side, or back-scatter mode or it may even be collected in an integrating nepholometer mode wherein scattered photons from essentially all directions are collected. For illustration, we choose a practical embodiment of 90 degree side scatter shown in FIG. 1. The detection signals v(t) 122 are approximately of the same form for all scattering directions.

Recalling that the particle 111 is small compared to the laser beam waist 202, we may now describe the pulse train that results when the scattering volume 109, as represented in cross-section by beam waist 202, is scanned across a particle at several positions A, B, C, etc., 206 along its trajectory 205.

As the particle 111 in FIG. 4 moves downward into the low-intensity "wings" of the Gaussian beam waist 206, a signal v(A) 208 is produced and shown in FIG. 5. Upon reversing the scan direction, a second signal v(B) 209 is produced when the particle is at position B 206. One full scan period 210 later, third signal v(C) 211 is produced. This continues until the particle leaves the scattering volume 109 and produces v(D), v(E), v(F), v(G) shown in FIG. 5.

The Gaussian beam intensity profile 221 in the scattering volume 109 (FIG. 4) is directly exhibited as a Gaussian envelope 212 of the detection signal v(t) 122 (FIG. 4). Each scan signal has the general form 231 but note that the width is slightly smaller at position A than D, 206, FIG. 3.

Note that the alternating v(t) 122 pulses are equally spaced at one scan period 210. Adjacent pulses are spaced between 0 and one full scan period; their spacing is one-half the scan period only if the particle trajectory is in a vertical plane containing the flow cell 108 centerline 133 and bisecting the scan extremities 131, 132.

Note that the pulse train has the form of so-called "sampled data" wherein the Gaussian envelope 212 is sampled by the scan 231. It is now clear how the scanning scattering volume method increases volumetric sampling rate and permits covering 100% of the flow cell cross-section. We next explain how scanning the scattering volume enhances response function, provides velocity information and reduces minimum detectable particle size.

In FIG. 5, the pulse train of signals v(t) 122 is seen to lie within a Gaussian envelop 212 and rise from zero to a maximum 213 as the scattering volume multiply scans over the particle. This $v_1$ max 213 signal is evidently more uniquely associated with particles of a given size than if the particle moves randomly through a stationary scattering volume. In other words, a stationary beam detector may be "fooled" as to the size of a particle if it passes through the sides or wings of the stationary beam but the scan of the present invention eliminates this problem. This is what is meant by better or enhanced response function. In practice, it has beer found that second state signal processing can faithfully reconstruct the Gaussian envelope 212 and that good response function results obtain if 3 or more "hits" in the scanning scattering volume occur.

Referring again to FIG. 1, it will be appreciated that the signal $v_1$ (t) 122 may be considered to be a detection signal. This detection signal v(t) 122 is provided as an input to second signal processing within a microcomputer 141. The computer 141 monitors the digital form of $v_1$ (t) 122 for a train of pulses representing a particle. In the preferred embodiment, the computer 141 simply looks for signals above a threshold set such that light scattering from the smallest particle of interest exceeds it. Pulse trains above threshold are considered to represent a single particle. After receiving a pulse train and a pause or period of no signal for a selected duration, the computer assumes that it has received the entire pulse train representing a particle. The digital form of v(t) 122 has been recorded by the computer and it then determines the maximum voltage for each pulse. The maximum voltage of the Gaussian curve corresponds to particle size. Of course, the correlation between the v max of the Gaussian curve and particle size will vary from application to application and must be calibrated. In the preferred embodiment, once a calibration is obtained, an appropriate look-up table is provided in computer 141 so that it can directly and immediately output and store a particle size measurement as opposed to v max of the Gaussian curve.

In many aerosol measurement applications it is desired to measure not only concentration and size but also particle velocity. In FIGS. 3, 4, and 5, it is seen that as the particle moves more or less perpendicularly through the scan plane it is "hit" at positions A, B, C, etc. 206 at approximate time interval ta, tb, tc, etc (208, 209, 211, etc.) Since the scattered photon flux is proportional to the beam intensity, shown as typical Gaussian in FIG. 4, (221), it follows that the detection signals will lie within a Gaussian envelope as indicated in FIG. 5 (212) and as explained above. Now the width of this envelope is evidently a direct and absolute measure of the velocity component of the particle normal to the scan plane. We note that this velocity component in laminar flow is simply the local speed of the particle if the particle is moving normal to the scan plane. The speed is also equal to the speed of the fluid elements transporting the particle provided the particle is small and the fluid accelerations are small. In most microcontamination applications, the particles may indeed be assumed to move at fluid element speed. This single velocity component measurement may obviously be generalized to 2 or 3 components.

After the computer 141 of FIG. 1 calculates the design particle information, it is stored, transmitted to another computer, or is output through a display such as a printer 142. Preferably the computer 141 stores the count number and particle size and outputs the same information to the printer 142. The computer 141 is also preferably provided with the fluid flow rate through the flow cell 108 by providing the computer 141 with the size of, and pressure within, the flow cell 108 by manual input. Then, using the average velocity of the particles as the fluid velocity, the computer 141 also calculates, stores and outputs total fluid sampled and particle concentration in the fluid.

The first signal processing signal $v_1$ (t) 122 is illustrated in FIG. 1 without residual or noise signals. Residual signals are due to stray light or other "pick-up". Residual signals increase the minimum detectable particle size. Deleterious impacts of residual signals can usually be managed by thorough design and careful construction of the apparatus.

Noise signals are random and provide the ultimate limitations to detection of fine particles. The scanning scattering volume method enables reduction of another limitation compared to prior art stationary beam methods and apparatus.

Whereas the probability of occupancy of a microcontamination particle of interest in the scattering volume is very low, there is an extremely large number of gas (fluid) molecules present. These molecules scatter light also and this collective signal can be much larger than that from the rare single particles. It is not the large, everpresent, average molecular scatter signal that limits the minimum detectable particle size; the limitation is due to random noise produced by this steady photocurrent. For example, in shot-noise limited detection, a measure of the noise is the familiar equation $$i_n = (2*e*I*\text{delta } f)^{\frac{1}{2}}$$

where $i_n$ is the RMS noise current, e=electronic charge, I is the average photocurrent and delta f is the band-pass of the detection electronics.

Figure 6:
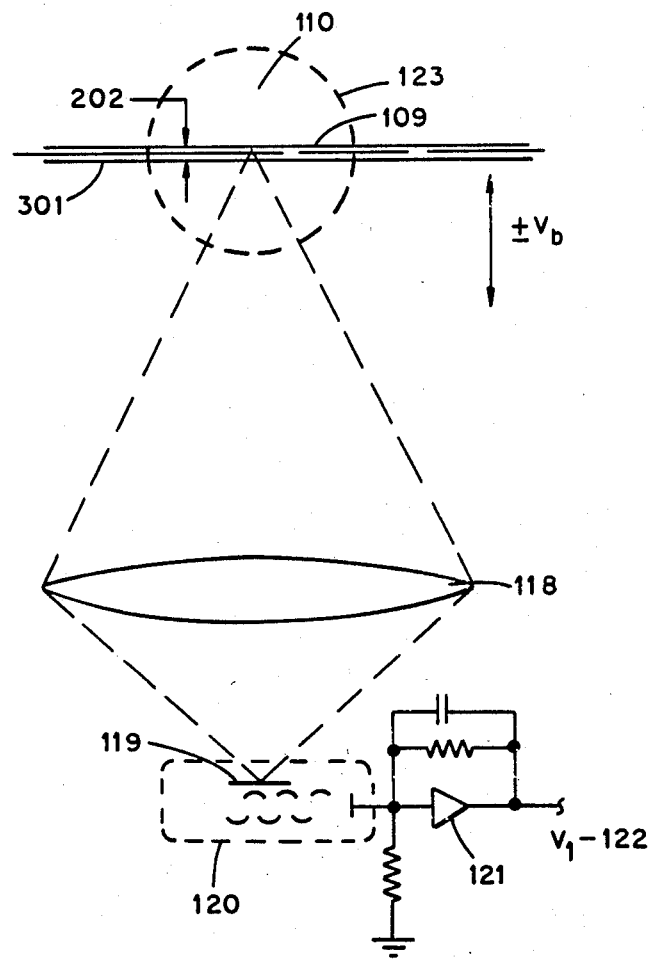
FIG. 6 is a somewhat schematic view of a particle detector that provides a realistic comparison between scanning and stationary scattering volumes.

We may now compare, by realistic order of magnitude, scanning and stationary scattering volumes designs. In FIG. 6 we assume that the laser power 301, laser beam diameter or waist 202=0.01cm 202, instantaneous scattering volume 109, fluid type and molecular concentration 110, collection optics 118, and detection electronics 119, 120, 121 are the same whether the scattering volume is stationary or scanning. We further assume that the minimum detectable particle size is limited by molecular scattering and that the particle concentration is low and randomly distributed over the flow cell cross section 123.

Given these assumptions, the present invention provides the following advantages:

1. The scanning scattering volume covers ~100% of the cross-section versus ~1% for a stationary scattering volume. Thus for a given fluid velocity, the scanning method has 100 times higher true volumetric sampling rate.

2. The response function for the scanning scattering volume is vastly superior to stationary beam devices; for a unique particle 111 size, a unique maximum signal v max 213 is produced. For the stationary beam, the voltage pulses are randomly and widely distributed from 0 to v max because they randomly cross the stationary scattering volume.

3. Scanning scattering volume designs have smaller minimum detectable particles since a larger signal (v max 213 versus an $v_1$ average lying between 0 and $v_1$ max 122.) is seen as a consequence of the multiple hits. Alternatively stated, the counting efficiency is higher.

It is further illustrative to note the futility of extending stationary beam art t handle microcontamination applications. Even if such lasers became available, beam power 100 times larger is required to cover 100% of the flow cell cross section 123. And worse, the molecular scatter and average photocurrent would increase 100-fold, thus increasing by 10-fold the minimum detectable particle size.

In summary, the preferred embodiment scans the beam of laser radiation and, thereby, the scattering volume over the particles of interest. This scanning scattering volume method enables design of particle counting apparatus which can advantageously provide count, concentration, size and velocity information. Other advantages over prior stationary beam art include up to 100% coverage of the flow cell cross section, higher volumetric sampling rate, enhanced response function, smaller minimum detectable particles and increased counting efficiencies.

While these specifications and disclosures explain the method by preferred embodiment, it is not the intention to limit the scope of the invention as defined by the appended claims.

We claim:

1. An apparatus for detecting particles in a fluid comprising:
    a sample volume;
    input means for admitting radiation into said sample volume;
    conduit means for directing a flow of fluid and particles in a path through said sample volume, said particles collectively having an average particle size and an average distance between adjacent particles;
    a source of radiation for producing a radiation beam having a cross-sectional dimension that is larger than the average particle size but is smaller than the average distance between adjacent particles;
    scanning means for producing a scanning beam from said radiation beam that moves between at least first and second scan positions at a scan rate;
    radiation directing means for directing the scanning beam through said input means into said sample volume and into the path of fluid and particles so that particles are hit by the scanning beam substantially one particle at a time and produce scattered radiation; and
    means for detecting the scattered light produced by the particles when hit by the scanning beam and for producing a detection signal substantially corresponding to at least one parameter of individual detected particles.

2. An apparatus for detecting particles in a fluid comprising:
    a sample volume;
    input means for admitting radiation into said sample volume;
    conduit means for directing a flow of fluid and particles in a path through said sample volume;
    a source of radiation for producing a radiation beam;
    scanning means for producing a scanning beam from said radiation beam that moves between at least first and second scan positions at a scan rate;
    radiation directing means for directing the scanning beam through said input means into said sample volume and into the path of fluid and particles so that particles are hit by the scanning beam and produce scattered radiation;
    means for detecting the scattered radiation produced by the particles when hit by the scanning beam and for producing a detection signal corresponding to the scattered radiation; and
    said radiation beam and the scan rate being chosen to be sufficiently large in relation to the flow velocity that a particle moving at the flow velocity will be hit by the scanning beam a plurality of times whereby the number of hits will correspond to the velocity component of the particle in a direction perpendicular to the scan direction.

3. An apparatus for detecting particles in a fluid comprising:
    a sample volume;
    input means for admitting radiation into said sample volume;
    conduit means for directing a flow of fluid and particles in a path through said sample volume;
    a source of radiation for producing a radiation beam;
    scanning means for producing a scanning beam from said radiation beam that moves between at least first and second scan positions at a scan rate;
    radiation directing means for directing the scanning beam through said input means into said sample volume and into the path of fluid and particles so that particles are hit by the scanning beam and produce scattered radiation;

means for detecting the scattered radiation produced by the particles when hit by the scanning beam and for producing a detection signal corresponding to the scattered radiation; and said radiation beam and the scan rate being chosen to be sufficiently large in relation to the flow velocity that a particle moving at the flow velocity will be hit by the scanning beam at least three times whereby the scattered radiation produced by three hits on a single particle defines a Gaussian curve corresponding to individual particle size.

4. The apparatus of claim 1 wherein said scanning means and radiation directing means produce a scanning beam with sufficiently large scan pattern to scan across substantially the entire sample volume.

5. The apparatus of claim 1 wherein said scanning means and radiation directing means provide a scanning beam that scans in a planar scan pattern that is oriented generally perpendicular to the fluid flow within said sample volume.

6. The apparatus of claim 1 wherein said radiation source comprises a laser and said scanning means comprises a scanning mirror.

7. An apparatus for measuring characteristics of particles in a fluid comprising:
   a flow cell;
   at least one window formed in said flow cell for admitting light;
   conduit means for directing a flow of fluid and particles in a flow path through said cell at a flow velocity;
   a light source for producing a light beam;
   an optical system for producing a scanning beam from said light beam that scans generally in a plane at a scan rate and for directing said scanning beam through said window into said cell in an orientation that places the plane of said scanning beam in a position generally perpendicular to the flow velocity of the fluid and particles, the volume inside said cell occupied by said light beam at an instant being defined as an instantaneous scattering volume and the volume inside said cell that is scanned by the scanning beam being defined as the scanning volume, the diameter of said scanning beam and the scan rate being chosen sufficiently large in relation to the flow velocity of the fluid and particles to result in the scanning beam multiply scanning over individual particles while passing through the scanning volume; and
   means for detecting the scattered light produced when a particle is multiply scanned by said scanning beam and producing a detection signal corresponding to the scattered light.

8. The apparatus of claim 7 further comprising analyzing and recording means for analyzing the detection signal to produce data corresponding to the particle and for recording said data.

9. The apparatus of claim 7 further comprising analyzing and recording means for analyzing the detection signal to project a Gaussian curve based on the light scattered by a single particle when multiply scanned by the scanning beam, calculating size data corresponding to the size of the particle based on said Gaussian curve, and recording at least the size data.

10. The apparatus of claim 7 further comprising analyzing means for analyzing the detection signal to determine velocity data of a single particle based upon the number of times a particle is scanned as it passes through the scanning volume and to produce a signal corresponding to the velocity data.

11. The apparatus of claim 7 further comprising analyzing and recording means for analyzing the detection signal to project a Gaussian curve based upon the light scattered by a single particle when multiply scanned by the scanning beam calculating size data corresponding to the size of the particle based on the Gaussian curve, determining velocity data of a single particle based upon the number of times a particle is scanned as it passes through the scanning volume and recording at least the size data and velocity data for each particle that passes through the scattering volume.

12. The apparatus of claim 7 further comprising analyzing and recording means for analyzing the detection signal to project a Gaussian curve based on the light scattered by a single particle when multiply scanned by the scanning beam and calculating velocity data of the particle based on the size of the Gaussian curve.

13. The apparatus of claim 7 wherein said light source is a laser.

14. A method for detecting information corresponding to particles in a fluid comprising:
   forming a beam of electro-magnetic radiation into an instantaneous scattering volume;
   scanning said instantaneous scattering volume through space between at least first and second positions to define a scanning volume;
   transporting particles by fluid means through the space defined as the scanning volume;
   multiply scanning the instantaneous scattering volume over individual particles while the particles are passing through the scanning volume;
   providing fluid conduit and window means to transport the fluid and particles and to transmit the radiation beam into the space defined as the scanning volume and to transmit scattered radiation out of the scanning volume; and
   collecting and detecting radiation from the particles within the scanning volume to produce a detection signal containing information relating to the particles.

15. The method of claim 14 further comprising analyzing the detection signal to determine particle size.

16. The method of claim 14 further comprising analyzing the detection signal to determine particle velocity.

17. The method of claim 14 further comprising analyzing the detection signal to reconstruct a Gaussian curve defined by the radiation produced by multiple scans over a single particle and determining size data from said Gaussian curve corresponding to the size of the individual particle.

18. The method of claim 14 further comprising analyzing the detection signal to determine the velocity of individual particles based upon the number of times a particle is scanned as it passed through the scanning volume.

19. The method of claim 14 further comprising analyzing the detection signal to reconstruct a Gaussian curve defined by the radiation produced by multiple scans over a single particle and determining velocity data from said Gaussian curve corresponding to the size of the individual particle.

* * * * *